United States Patent
Nakanishi et al.

[11] Patent Number: 6,042,708
[45] Date of Patent: Mar. 28, 2000

[54] MICROCHIP ELECTROPHORETIC METHOD AND APPARATUS

[75] Inventors: Hiroaki Nakanishi, Nara; Akihiro Arai; Yosuke Iwata, both of Kyoto, all of Japan

[73] Assignee: Shimadzu Corporation, Kyoto, Japan

[21] Appl. No.: 08/949,433

[22] Filed: Oct. 14, 1997

[30] Foreign Application Priority Data

Oct. 31, 1996 [JP] Japan .................................... 8-307055

[51] Int. Cl.⁷ ........................ G01N 27/26; G01N 27/447
[52] U.S. Cl. ........................ 204/452; 204/602; 204/603; 356/344
[58] Field of Search ................... 204/452, 603, 204/612, 602, 455; 356/344

[56] References Cited

U.S. PATENT DOCUMENTS

| | | |
|---|---|---|
| 5,061,362 | 10/1991 | Gordon . |
| 5,395,502 | 3/1995 | Pawliszyn . |
| 5,627,643 | 5/1997 | Birnbaum et al. . |
| 5,784,154 | 7/1998 | Pawliszyn . |

FOREIGN PATENT DOCUMENTS

| | | |
|---|---|---|
| 0 665 430 | 8/1995 | European Pat. Off. . |
| WO 93/14389 | 7/1993 | WIPO . |
| 94/20843 | 9/1994 | WIPO . |
| WO 97/30347 | 8/1997 | WIPO . |

OTHER PUBLICATIONS

*FAN Z. H. et al.* "Micromachining of Capillary Electrophoresis injectors and seperators on glass Chips and Evaluation of Flow at Capillary Intersections" Analytical Chemistry, vol. 66, No. 1–Jan. 1. 1994, pp. 177–184.

*ZHU R. et al.* "Post–Column Reaction System for Fluorescence Detection in Capillary Elecrophoresis" Journal of Chromatography–vol. 716, No.1, Nov. 17, 1995, pp. 123–126.

*Primary Examiner*—William H. Beisner
*Attorney, Agent, or Firm*—Armstrong, Westerman, Hattori, McLeland & Naughton

[57] ABSTRACT

In order to irradiate a constant range of a separation passage of a microchip, light from a light source linearly extending along the separation passage is transmitted through a cylindrical lens and a bandpass filter and introduced into the separation passage. The light transmitted through the separation passage of the microchip is introduced into a photocell array through a cylindrical lens and detected. Measurement is repetitively performed and accumulated to determine migration patterns.

11 Claims, 7 Drawing Sheets

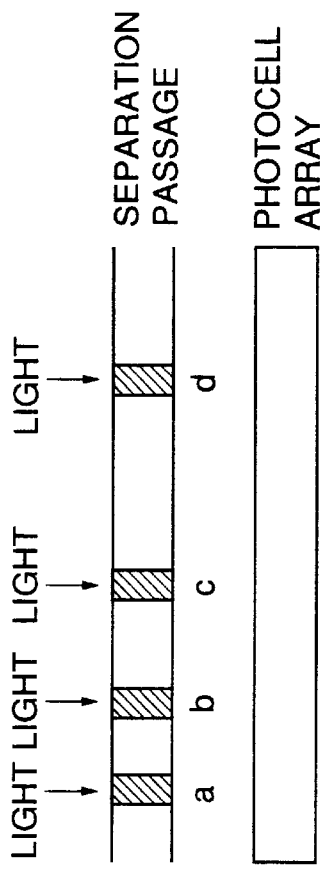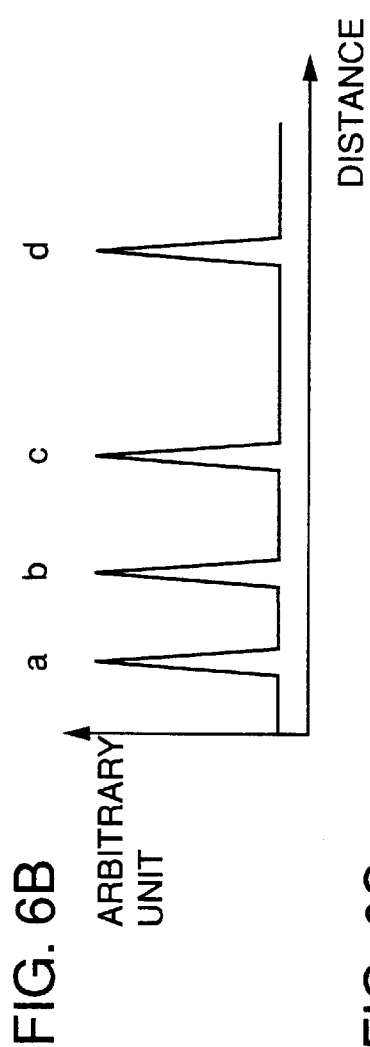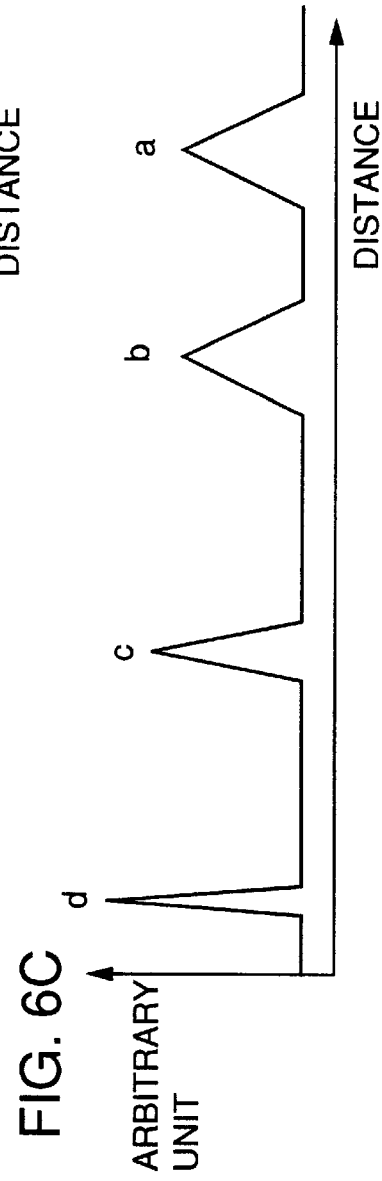

MICROCHIP ELECTROPHORETIC METHOD AND APPARATUS

BACKGROUND OF THE INVENTION

1. Field of the Invention

The present invention relates to a method of analyzing a very small quantity of a wide range of analytes, especially biopolymers such as proteins or nucleic acids at high speed and in high resolution, and is an apparatus for this purpose. More particularly, it is an apparatus that relates to a microchip electrophoretic method that employs a microchip. The microchip is prepared by forming a groove for feeding a liquid onto the surface of at least one of a pair of transparent plate members. The other plate member is provided with holes in positions corresponding to the groove. These plate members are adhered to each other while positioning the groove inward, thereby forming a separation passage by means of the groove. By filling up the separation passage with a migration liquid, injecting a sample into one end of it, and applying a migration voltage across the separation passage, the sample is electrophoresed in the separation passage.

2. Description of the Background Art

In the case of analyzing a very small quantity of protein or nucleic acid, an electrophoretic apparatus, such as a capillary electrophoretic apparatus, is generally employed. In the capillary electrophoretic apparatus, a migration buffer is filled in a glass capillary having an inner diameter of not more than 100 $\mu$m. A sample is introduced into one end, followed by the application of a high voltage across the capillary for migrating the analyte in the capillary. The capillary, having a large surface area with respect to its volume, i.e., having high cooling efficiency, allows application of a high voltage, and can analyze a very small quantity of sample, such as DNA, at high speed in high resolution.

However, the capillary is fragile due to its small diameter even though it is usually protected by a polyimide coating. Therefore, the user must be extremely careful when exchanging capillaries. For this reason a capillary electrophoretic chip, called a microchip, has been proposed. This microchip is formed by connecting two substrates, as described in D. J. Harrison et al., Anal. Chim. Acta 283 (1993), pp. 361 to 366. FIGS. 1A to 1C show an example of such a microchip. This microchip consists of a pair of transparent substrates (such as glass plates) 51 and 52. Intersecting electrophoretic capillary grooves 54 and 55 are formed on a surface of substrate 52, while reservoirs 53 are provided on substrate 51 as holes in positions corresponding to the ends of grooves 54 and 55 respectively.

When employing this microchip, substrates 51 and 52 are overlapped, as shown in FIG. 1C, so that an electrophoretic buffer solution is injected into grooves 54 and 55 from any reservoir 53. Subsequently, a sample is injected into reservoir 53, corresponding to one end of shorter groove 54, while a pair of electrodes are inserted between reservoirs 53, corresponding to both ends of groove 54, for applying a high voltage to the sample injection at a prescribed time. In this way, the sample is dispersed into groove 54.

Then, another pair of electrodes are inserted between reservoirs 53, corresponding to both ends of longer groove 55, for applying a migration voltage. The sample, which is present on intersection 56 between grooves 54 and 55, is electrophoresed in groove 55. A detector such as an ultraviolet visible light photometer, a fluorescent photometer, or an electrochemical detector, is located in a correct position to groove 55, for detecting separated components.

Conventional microchip electrophoretic apparatuses employing optical detectors for the detection of constituents use laser induced fluorescence detection as a detection means. No apparatus performs detection by absorption in an ultraviolet visible region. If ultraviolet visible absorption detection is to be applied, it is conceivable as a method of introducing incident light perpendicularly to a passage and detecting target components passing through a certain specific position of a detection part through means such as a photocell, thereby confirming separation in a similar way to a conventional capillary electrophoretic apparatus.

When light is introduced into a microchip perpendicularly to its surface as in case of capillary electrophoresis, an optical path length of only about 20 $\mu$m can be obtained and this is about ⅖ of that in conventional capillary electrophoresis. Also in the conventional capillary electrophoresis, the optical path length (about 50 $\mu$m) is so short that its inferior sensitivity is a serious drawback despite its high resolution. Although it is conceivable to swell a passage of a cell part in order to increase the optical path length, as observed in a bubble cell or the like, it is still difficult to implement a sufficient optical path length.

SUMMARY OF THE INVENTION

Accordingly, the present invention is meant to improve detection sensitivity in microchip electrophoresis.

The microchip electrophoretic, method introduced by the present invention is adapted to fill up a separation passage of a microchip with an electrophoretic buffer solution, inject a sample into its one end and apply a migration voltage across the separation passage, thereby performing electrophoresis to the sample in the separation passage, and comprises the following steps:

(a) Stopping application of the migration voltage upon complete separation of target components in the sample;

(b) Irradiating the separation passage with light over a prescribed range in which the target components are separated and repetitively measuring absorption or light emission by the sample over the entire range; and (c) Accumulating measured values in each position of the separation passage, thereby obtaining migration patterns.

The microchip electrophoretic apparatus introduced in the present invention comprises a microchip, a high voltage power supply unit, light irradiation means, light detection means and a data processing/control part. The microchip has a separation passage formed in a transparent member and is filled with a buffer solution. Sample is injected into one end and a migration voltage is applied across the separation passage for electrophoresis and separating the sample in the separation passage. The high voltage power supply unit applies the migration voltage across the separation passage. The light irradiation means irradiates the separation passage with light over a prescribed range. The light detection means detects absorption of the light or light emission by sample components separated in the separation passage. The data processing/control part controls the migration power supply unit for stopping the application of the migration voltage upon complete separation of target components in the sample. It repetitively performs measurements along the separation passage by the light detection means in this state, accumulating measuring signals in each position of the separation passage for obtaining migration patterns and thereafter performing data processing.

An exemplary microchip comprises a pair of transparent plate members. A groove for feeding a liquid is formed on a surface of at least one of the plate members, the other plate member is provided with holes in positions corresponding to the groove, and these plate members are joined while directing the groove inward, forming a separation passage by the groove.

In order to obtain migration patterns along the separation passage while stopping application of the migration voltage, the light irradiation means comprises a light source and an optical system irradiating a prescribed range of the separation passage with linearly condensed light. The light detection means comprises a plurality of photodetectors which are arranged along the separation passage for simultaneously detecting light from sample components in the separation passage which have been irradiated with the light by the light irradiation means. The data processing/control part repetitively performs measurements by the light detection means, accumulating the measuring signals in each photodetector.

In an actualized structure, the light irradiation means comprises a light source which extends linearly along the separation passage, and a cylindrical lens, which is positioned for condensing light widthwise along the separation passage and for introducing light from the light source into the separation passage. The light detection means comprises a cylindrical lens that is positioned for condensing light widthwise along the separation passage and for guiding light from the separation passage to the photodetectors.

In order to obtain migration patterns along the separation passage while stopping application of the migration voltage, the light irradiation means comprises a light source and an optical system irradiating the separation passage with light beam. The light detection means comprises a single photodetector, which is positioned to detect light from the sample in the separation passage by light from the light irradiation means. A set, which includes the light irradiation means and the light detection means, and the microchip, are capable of relative movement along the separation passage. The data processing/control part repetitively moves this set or the microchip along the separation passage for accumulating detection signals by the light detection means in each position of the separation passage.

The light detection means is adapted to detect light absorption by sample components in the separation passage. Either the light irradiation means or the light detection means comprises spectroscopic means selecting a wavelength for measuring absorbancy.

The number of repetitive measurement times for the gathering of information is preferably automatically calculated and controlled by the data processing/control part. To this end, the data processing/control part comprises a calculation formula which includes a diffusion coefficient of the sample and a peak deterioration degree as parameters for calculating the number of repetitive measurement times by light irradiation in the separation passage, and automatically calculates the number of repetitive measurement times and controls the repetitive measurement by inputting such parameters.

As to a concrete example for calculating the number of repetitive measurement times, the data processing/control part comprises the following calculation formula for obtaining a time t' up to deterioration of a theoretical plate number to N' as a time allowing repetitive measurement.

$$t'=(L^2/N'-\sigma^2)/2D$$

The data processing/control part calculates the number of repetitive measurement times on the basis of the time t'. In the above formula, L represents a length of the separation passage (capillary), σ represents a standard deviation of the peak, and D represents the diffusion coefficient.

In another example for calculating the number of repetitive measurement times, the data processing/control part comprises the following calculation formula for obtaining a time t' up to deterioration of a theoretical plate number to N' as a time allowing repetitive measurement.

$$t'=L^2(1/N'-1/N)/2D$$

And the data processing/control part calculates the number of repetitive measurement times on the basis of the time t'.

When the migration voltage applied across the separation passage is eliminated after complete separation of the target components, no inertial force acts on the separated components dissimilarly to the liquid chromatography; the components are naturally diffused and remain in the passage. The light detection means repetitively measures absorption by light applied to the overall passage or fluorescence in this state. The position of each photodetector of the light detection means corresponds to that of the passage, and hence the light intensity at each position of the passage is measured and repetitively accumulated. While the components in the passage are naturally diffused during the measurement, the signal-to-noise ratio is 17.3, assuming that it takes about 2.5 seconds for deterioration of the peak shape by about 90% in terms of the theoretical plate number. Accumulation is performed 300 times in this period, as described later.

In the conventional method of providing a detector on a part of a separation passage for detecting target components passing through this position, the analysis is not completed until separation is completed and the final target component passes through this position. In the present invention, on the other hand, measurement can be executed at the point of time when the final target component is completely separated, thereby shortening and the measuring time.

It is possible to improve the signal-to-noise by repeating the measurement and accumulating the measured values, whereby the detection sensitivity is improved.

While the peak width of an electropherogram is increased as the migration speed is reduced in the conventional detection method, all target components are at the same migration time and hence an elegant electropherogram can be obtained with regular peak widths by means of the present invention.

Because the number of repetitive measurement times is automatically calculated, it is not necessary to manually perform complicated calculations and therefore erroneous operation is not caused by miscalculation.

The foregoing and other objects, features, aspects and advantages of the present invention will become more apparent from the following detailed description and accompanying drawings.

BRIEF DESCRIPTION OF THE DRAWINGS

FIG. 6A is a schematic front elevational view showing a separation passage stopping separation and a photocell array in the embodiment, FIG. 6B is a waveform diagram showing a chromatogram of the embodiment, and FIG. 6C is a waveform diagram showing an electropherogram of the prior art.

DESCRIPTION OF THE PREFERRED EMBODIMENTS

Figure 1A:
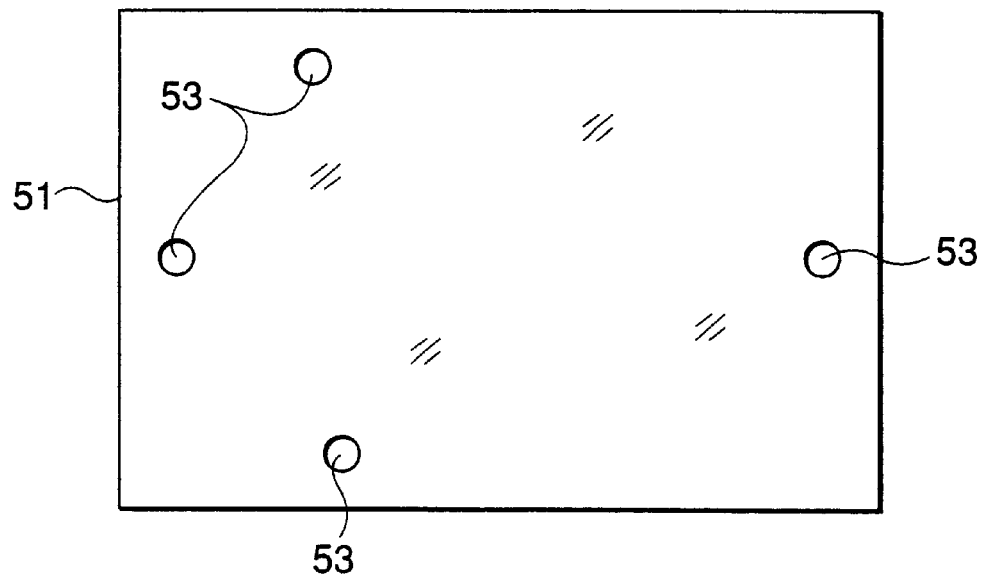
FIGS. 1A and 1B are plan views showing transparent plate members forming a microchip according to each of the prior art and the present invention.
Figure 1B:
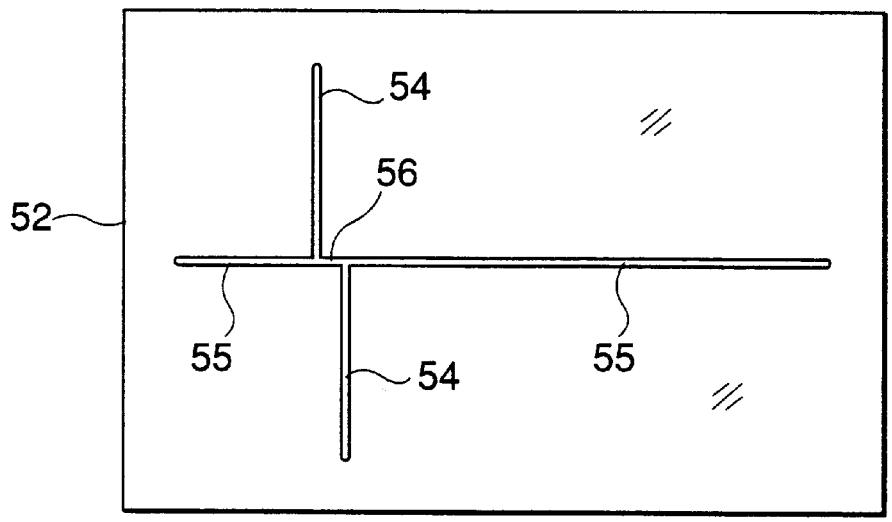
Figure 1C:
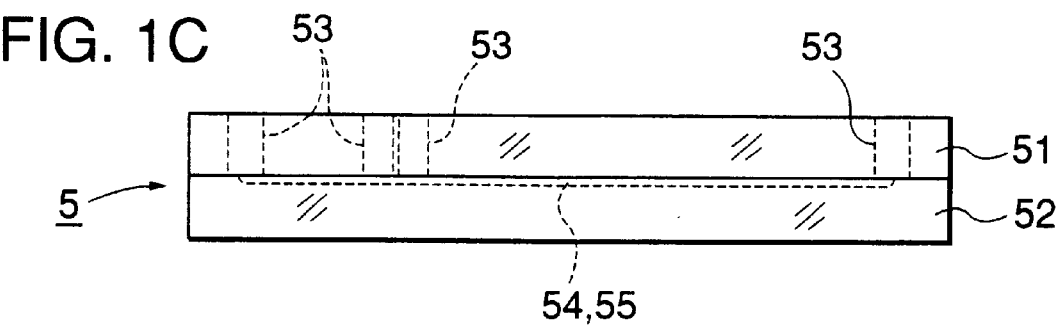
FIG. 1C is a front elevational view showing the assembled microchip.
Figure 2:
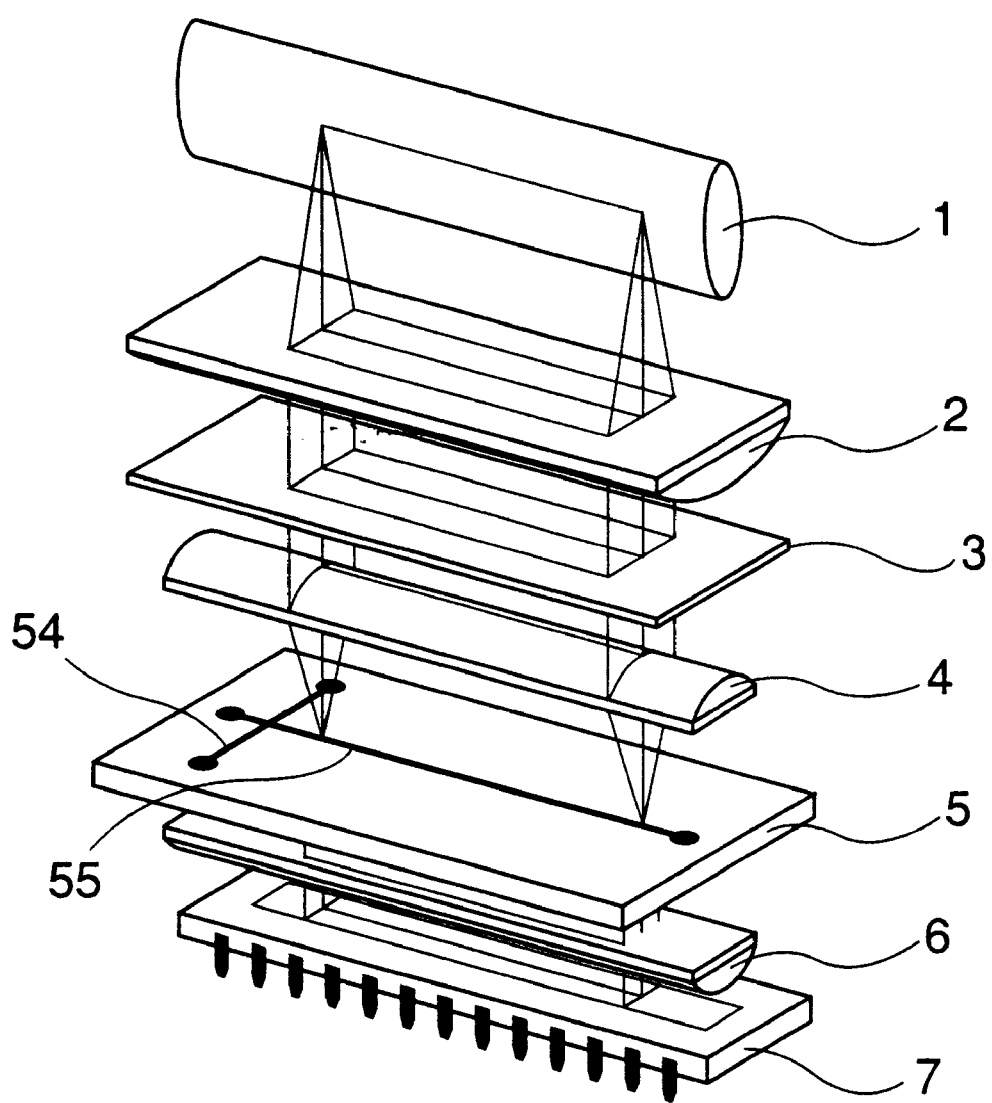
FIG. 2 is a schematic perspective view showing an embodiment of the present invention.

FIG. 2 shows an apparatus according to an embodiment of the present invention. Microchip 5 is that shown in FIG. 1C. In order to irradiate a constant range of its separation passage 55, light from a light source 1 is linearly extended along separation passage 55 and is converted to parallel light by cylindrical lens 2. Introduced into bandpass filter 3, the light transmitted through bandpass filter 3 is made to have a prescribed wavelength, is condensed by cylindrical lens 4, and introduced into separation passage 55 of microchip 5. Cylindrical lens 6 is provided on an opposite side of microchip 5 in order to condense the light transmitted through separation passage 55, and the light condensed by cylindrical lens 6 is introduced into photocell array 7 of a light detector and detected. Cylindrical lenses 2, 4 and 6, bandpass filter 3 and photocell array 7 are shorter than, but substantially identical in length to separation passage 55. Photocell array 7 comprises 512 photodiodes, which are linearly arranged along the longitudinal direction of separation passage 55 as detection elements.

Bandpass filter 3, which is arranged on the light irradiation side in this embodiment, may alternative arranged on the light detection side, i.e., on the optical path between microchip 5 and photocell array 7.

Figure 3:
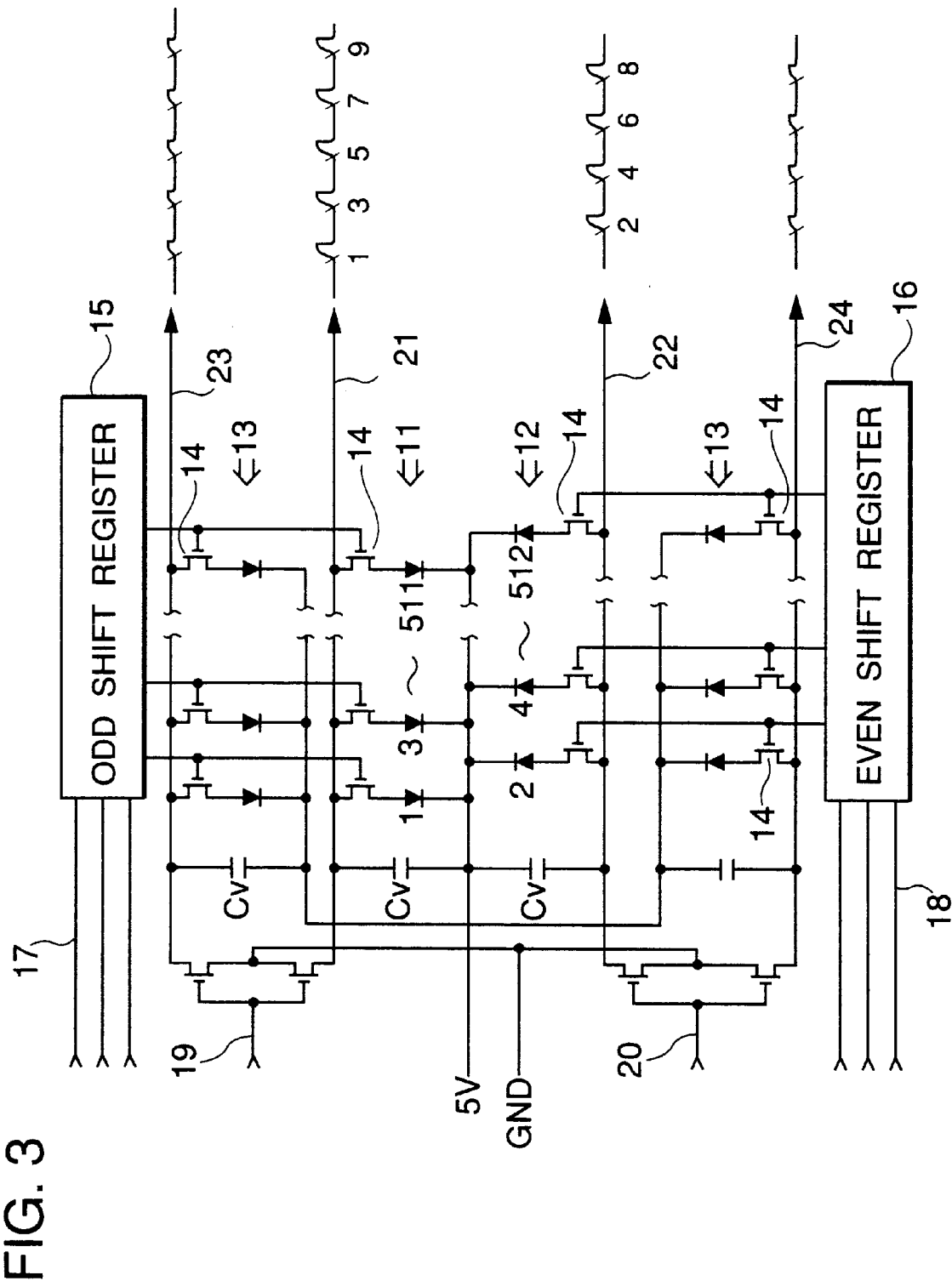
FIG. 3 is a circuit diagram showing a photocell array in the embodiment.

Photocell array 7 has a circuit structure shown in FIG. 3. Photocell array 7 has odd photodiodes 11 and even photodiodes 12, which are alternately arranged on single straight lines. The number of photodiodes 11 and 12 is 512 in total. Photocell array 7 is further provided with 512 dummy photodiodes 13, which have the same characteristics as photodiodes 11 and 12 employed for measurement. Switching elements 14 consisting of MOS-FETs are connected to photodiodes 11, 12 and 13 respectively. An odd shift register 15 or an even shift register 16 is connected to each switching element 14, so that ON and OFF states of each switching element 14 are switched by a signal from shift register 15 or 16.

Numerals 17 and 18 denote operating signal input terminals of the odd and even shift registers 15 and 16 respectively, numerals 19 and 20 denote odd and even reset signal input terminals respectively, numerals 21 and 22 denote output terminals for the odd and even photodiodes 11 and 12 respectively, numerals 23 and 24 denote output terminals for the dummy photodiodes 13, and symbol Cv denotes capacitors.

Figure 4:
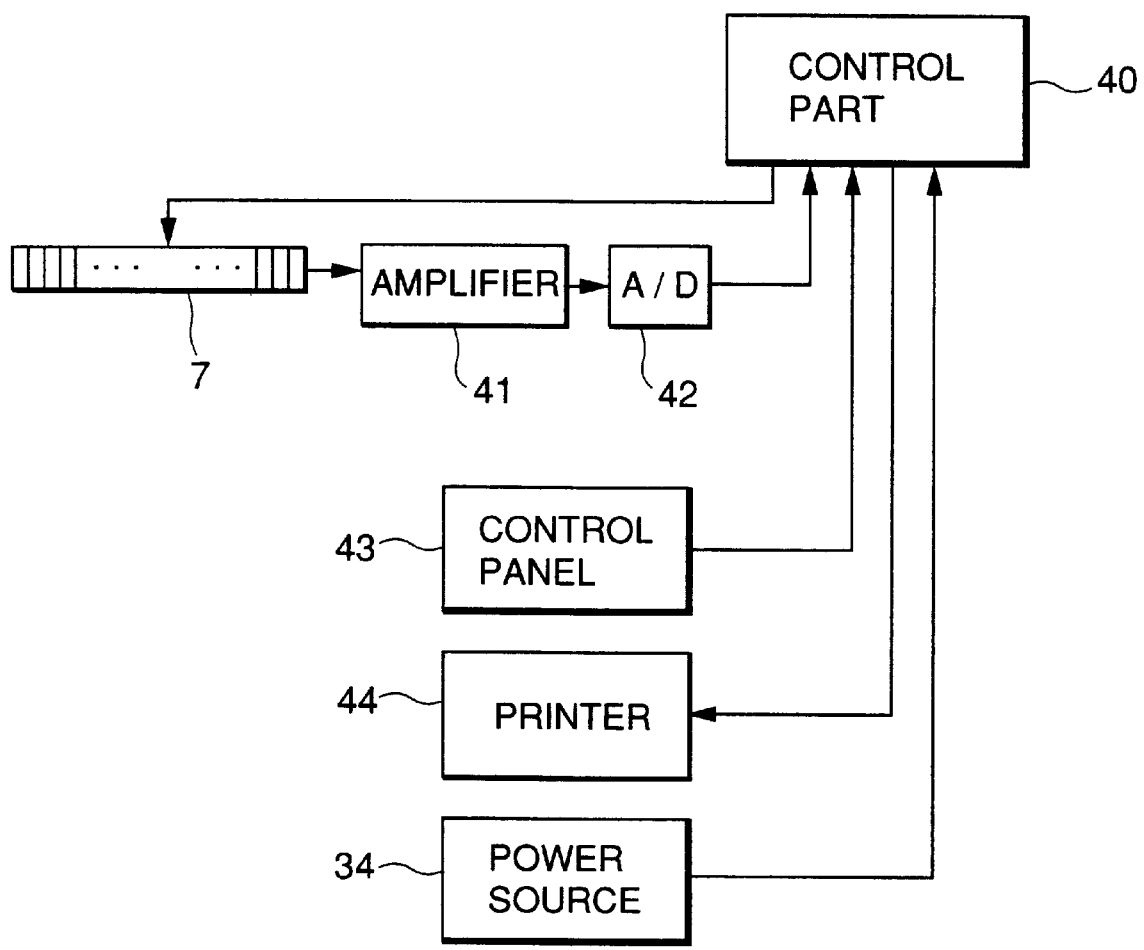
FIG. 4 is a block diagram showing a control system in the embodiment.

The electrophoretic apparatus comprises control part 40 shown in FIG. 4, which controls this electrophoretic apparatus. Control part 40 is formed by a microcomputer including a CPU, a RAM, and a ROM. Input terminals 17 to 20 of photocell array 7 are connected to control part 40. Output terminals 21 to 24 of photocell array 7 are connected to control part 40 through amplifier 41 and A-D convertor 42. Furthermore, control panel 43 comprising keys for an operator for inputting commands and a CRT (cathode ray tube) for making displays, X–Y printer 44 for charting measurement results and power source 34 are connected to control part 40.

In this embodiment, the light from light source 1 is converted to parallel light by cylindrical lens 2, passes through bandpass filter 3 to be converted to light of only a specific wavelength, and is condensed on separation passage 55 of microchip 5 by cylindrical lens 4. The light passing through separation passage 55 is converted to parallel light again by cylindrical lens 6, and applied to photocell array 7.

Figure 5:
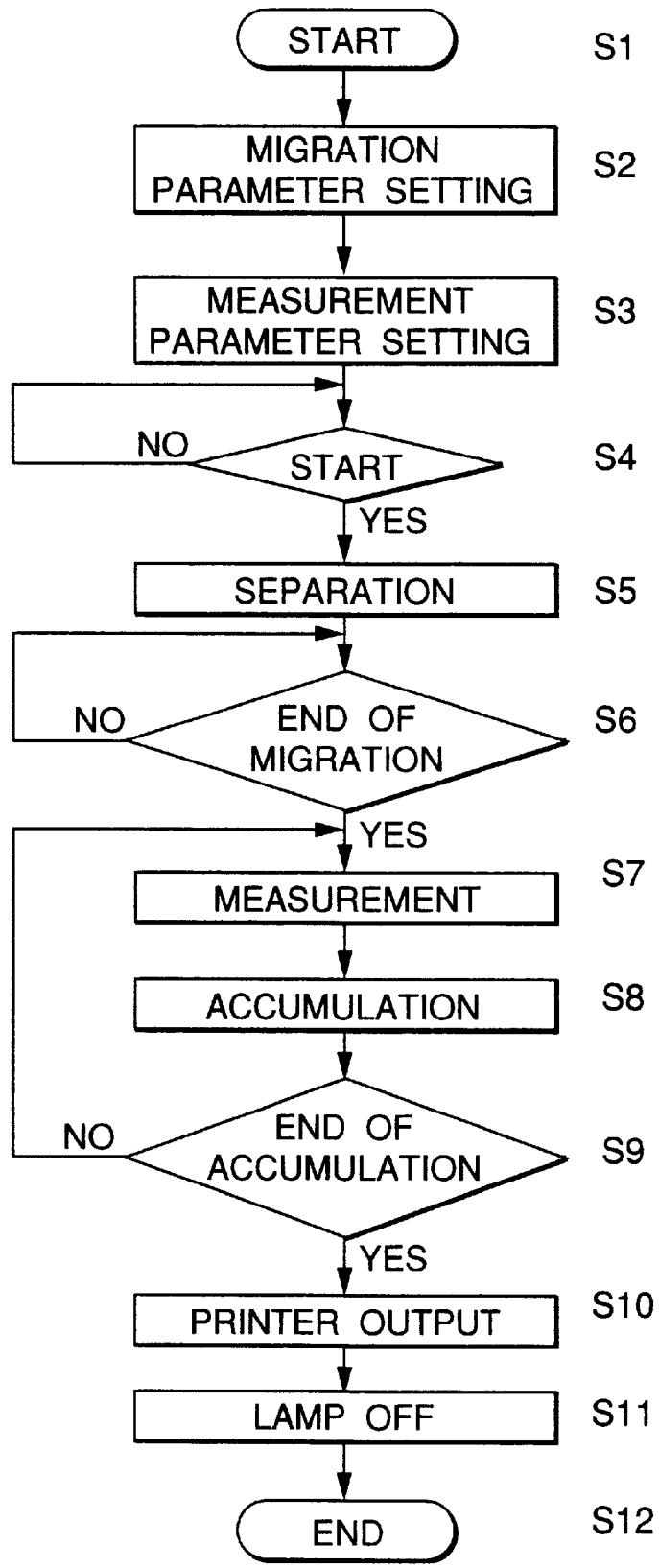
FIG. 5 is a flow chart showing operations of the embodiment.

Operations of this embodiment are described with reference to a flow chart shown in FIG. 5.

When a program is started, initialization is performed for bringing power source 34 into an ON state and setting printer 44 on an initial position (step S1). The operator sets separation parameters, such as a sample injection time, a sample injection voltage, and a migration voltage through control panel 43 (step S2). The operator then sets measurement parameters, such as a migration end time (=accumulation start time) and an accumulation time (step S3). The program waits for a start command (step S4).

As in conventional microchip electrophoresis, the operator injects a sample and pushes down a start button of control panel 43. Electrophoretic separation of the sample is begins in, and the migration voltage is applied across separation passage 55 of the microchip 5 based on the parameters which have been set in the program (steps S4 and S5). With this, the sample is moved into separation passage 55 and separated.

When the set migration time has ended (step S6), target components are separated in separation passage 55. It is assumed that target components a, b, c and d are separated as shown in FIG. 6A. Capillary electrophoresis (identical to this microchip electrophoresie is characterized by the fact that when a high voltage applied for electrophoresis is eliminated, components in a capillary remain in situ with no influence by inertial force. Therefore, the components a, b, c and d are naturally diffused. Measurement is started in accordance to the setting at the step S3 (step S7). At this time, each photodiode of photocell array 7 corresponds to each position of passage 55. Photocell array 7, which is provided with the 512 photodiodes arranged at pitches of 25 $\mu$m, is 12.8 mm in length. Accordingly, light absorption images are obtained in the resolution of 25 $\mu$m in the range of the length of 12.8 mm of the separation passage 55. The states of separation shown in FIG. 6A are obtained as ultraviolet absorption images shown in FIG. 6B.

Control part 40 repetitively scans photocell array 7 and makes accumulation, whereby a signal-to-noise ratio shown in FIG. 6B is rapidly increased (steps S7, S8 and S9). When the accumulation is completed, control part 40 outputs the measurement results to printer 44 (step S10), and turns off power source 34 for ending the program (steps S11 and S12).

The time for repetitive measurement can be decided with a standard of the degree of deterioration of a theoretical plate number N. The theoretical plate number N, at the time of stopping electrophoresis, is deteriorated by natural diffusion. If stopped with a deterioration of 10%, for example, scanning can be performed about 300 times, assuming that there is a repetition time of 2.5 sec. and single scanning takes 8 msec. (as described later,) and the signal-to-noise ratio is increased by 17.3 times. The signal-to-noise ratio is further improved in the case of scanning at a higher speed or analyzing components having small diffusion coefficients.

FIG. 6C shows an electropherogram obtained by detecting target components passing through a specific position of a detection part in conventional capillary electrophoresis. As compared with that shown in FIG. 6B, the signal-to-noise ratio is smaller, the measurement time is longer, and peak widths of components having slow migration speeds are larger.

The number of repetitive measurement times allowable after stopping the application of the migration voltage is described.

In general, the theoretical plate number N is expressed by a capillary (separation passage) length L and a standard deviation σ of peaks as follows:

$$N = (L/\sigma)^2 \quad (1)$$

Assuming that the capillary length L is 2 cm and the theoretical plate number N is 10000, $$\sigma^2 = 4/10000$$
$$= 1/2500$$

A theoretical plate number N' after t' seconds from stopping the application of the migration voltage can be expressed as follows:

$$N' = L^2/(\sigma^2 + \sigma'^2) \quad (2)$$

where σ' represents standard deviation of the peaks after t' seconds from stopping the application of the migration voltage. Assuming that D represents a diffusion coefficient and t represents time, natural diffusion of a solute in a solvent is expressed as follows:

$$\sigma^2 = 2Dt \quad (3)$$

Hence, $$N' = L^2/(\sigma^2 + 2Dt') \quad (4)$$

Hence, the time before deterioration of the theoretical plate number N to the value N', i.e., the time t' during which repetitive measurement is possible before the deterioration of the theoretical plate number N to the value N' is as follows:

$$t' = (L^2/N' - \sigma^2)/2D$$

When the time t' during which repetitive measurement is possible is obtained, the number of scan times is easily calculated since the time required for a single scan of the photocell array 7 is obvious.

Table 1 Illustrates times before reduction to (N'/N) of theoretical plate numbers of some solute examples.

It is known that a solute in a solvent causes only natural diffusion when a migration voltage is eliminated during migration in capillary electrophoresis. In the case of scanning ultraviolet absorbance measurement in parallel with separation passage 55 while eliminating the applied voltage, improvement of the signal-to-noise ratio is expected in response to the number of scan times. When a photodiode array detector for a high-speed liquid chromatograph is employed, as the photocell array 7, the time required for scanning is 8 msec. A solute having ultraviolet absorption generally has a molecular weight of at least 100, and the theoretical plate number N of such a solute is not deteriorated to more than 90% for at least 2.5 seconds. Assuming that scanning is performed 300 times in 2.5 seconds, noise n', which is reached by scanning 300 times, can be expressed in relation to noise n of the measurement of a single scanning, as follows:

$$N' = n/(300)^{1/2}$$
$$= n/17.3$$

Hence, improvement of the signal-to-noise ratio of 17.3 times can be expected.

Figure 7:
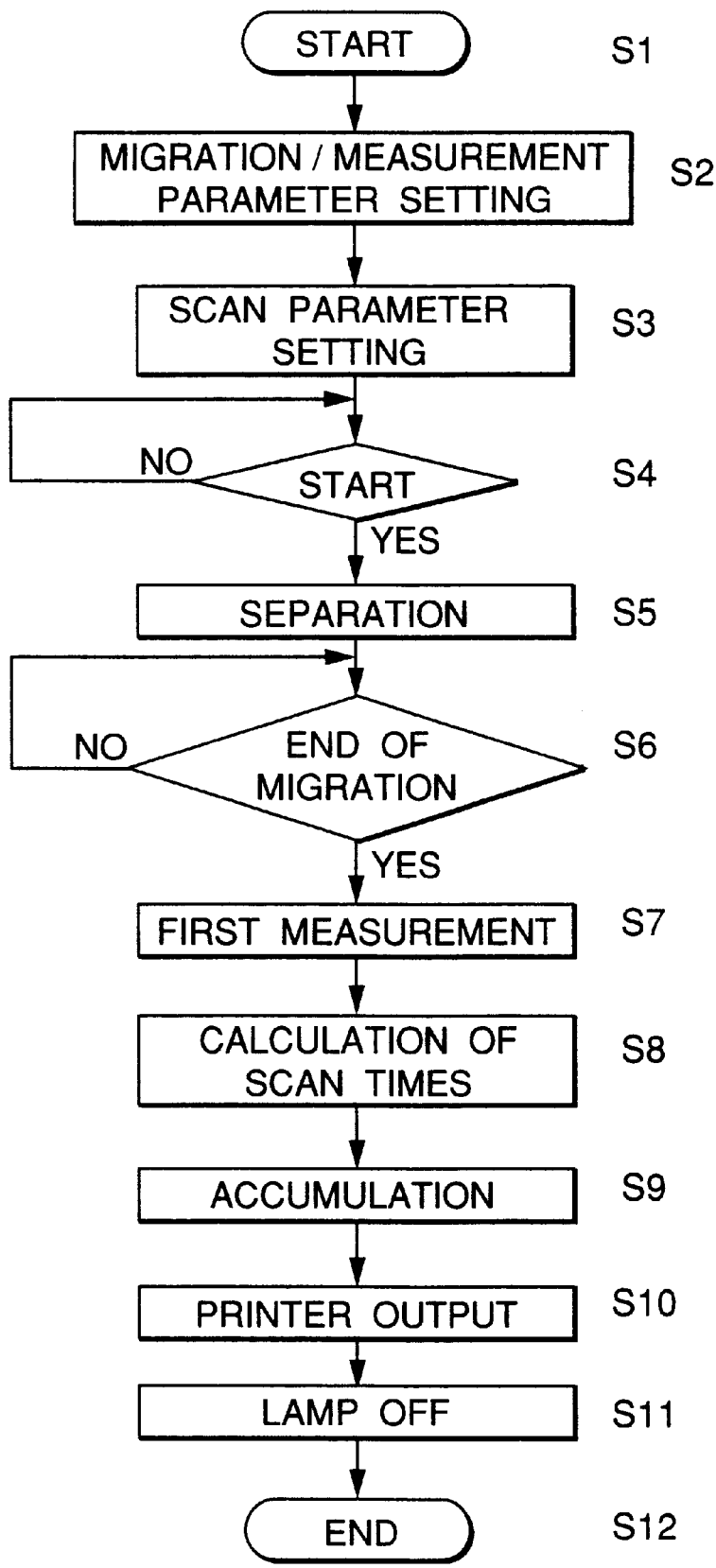
FIG. 7 is a flow chart showing operations in another embodiment of the present invention.

When the repetition time is obtained by substituting numerical values for the parameters in the expression (5), the number of scan times can be decided. However, this calculation is complicated, and requires lengthy manual calculation by the operator before measurement, which may result in erroneous manipulation caused by miscalculation. According to another preferred embodiment of the present invention, the expression (5) is stored in control part 40, which is a computer for automatically performing this calculation by simply inputting necessary parameters in control part 40. Operations performed at this time are described in the flow chart shown in FIG. 7.

When a program is started, initialization is performed for bringing power source 34 into an ON state and setting printer 44 to its initial position (step S1). The operator then uses control panel 43 (step S2) to set the separation parameters, which include the sample injection time, the sample injection voltage and the migration voltage. Also included are the measurement parameters for the migration end time (=accumulation start time) and the accumulation time.

The operator then inputs the parameters for deciding the number of scan times, i.e., the diffusion coefficient D, the capillary length L, and an allowable degree of deterioration (corresponding to the value N') of the theoretical plate number N caused by a wait time by the repetitive measurement (step S3). The program then waits for a start command (step S4).

TABLE 1

| Solute | Molecular weight | Concentration (mol/l) | D × 10⁵ (cm²/sec) | N'/N = 0.9 (sec) | N'/N = 0.8 (sec) | N'/N = 0.7 (sec) |
|---|---|---|---|---|---|---|
| Hydrogen chloride | 36.5 | 0.1 | 2.5 | 0.889 | 2.000 | 3.429 |
| Sodium chloride | 58.5 | 0.05 | 1.39 | 1.599 | 3.597 | 6.166 |
| Ethyl alcohol | 46 | dilute | 1 | 2.222 | 5.000 | 8.571 |
| Glycerin | 92 | 0.125 | 0.83 | 2.677 | 6.024 | 10.327 |
| Malt sugar | 342 | 0.1 | 0.42 | 5.291 | 11.905 | 20.408 |
| Serum albumin (bovine) | 70000 | dilute | 0.061 | 36.430 | 81.967 | 140.515 |
| Serum globulin (bovine) | 167000 | dilute | 0.04 | 55.556 | 125.000 | 214.286 |
| Urease | 480000 | dilute | 0.035 | 63.492 | 142.857 | 244.898 |
| Hemocyanin | 6600000 | dilute | 0.0138 | 161.031 | 362.319 | 621.118 |

Similar to general microchip electrophoresis, the operator injects the sample and pushes down the start button of control panel 43. Electrophoretic separation of the sample is started according to the program, and the migration voltage is applied across separation passage 55 of microchip 5 on the basis of the set parameters (steps S4 and S5). With this, the sample is moved into separation passage 55 and separated. When the set migration time is ended (step S6), target components are separated in separation passage 55.

Measurement in photocell array 7 is obtained by the following steps: first scanning is performed (step S7), and the standard deviation σ of sample peaks is obtained on the basis of the measurement results, and are used for calculating the number of scan times from the expression (5) (step S8). The photocell array 7 is repetitively scanned by the calculated number of scan times and the results are accumulated (step S9). After completion of the accumulation, measurement results are outputted to the printer 44 (step S10), and power source 43 is turned off, thus ending the program (steps S11 and S12).

From the relation of the expression (1), the expression (5) can be transformed as follows:

$$t' = L^2(1/N' - 1/N)/2D \qquad (5a)$$

In the calculation of the number of scan times during step S8, the theoretical plate number N of the sample peak may be obtained on the basis of the measurement results of the first scanning.

If the allowable degree of deterioration of the theoretical plate number N has been determined by the theoretical plate number N at the first measurement, and the length L of the separation passage 55 has been decided upon, the parameter inputted by the operator is only the diffusion coefficient D. Furthermore, the diffusion coefficient D can also be determined if a target sample and a solvent have been decided upon, whereby the number of scan times can be automatically calculated without inputting any parameter.

As still another embodiment, scanning for measurements can be repeated by providing light irradiation means of a measuring device with a light source and an optical system irradiating a separation passage with beamy light, providing light detection means with a single photodetector which is positioned to detect light from a sample in the separation passage by light from the light irradiation means. Either the light irradiation means and the light detection means are supported yet unfixed along the separation passage of a microchip, or the microchip is to be movable along the separation passage in respect to the light irradiation means and the light detection means. In the case of migrating giant molecules such as DNAs or using a gel liquid as a buffer solution, it is conceivable that diffusion (natural diffusion) of a sample hardly takes place, and the accumulation can be performed without high-speed scanning.

Although the present invention has been described and illustrated in detail, it should be understood that this is intended as an illustration and example only, and is not to limit the spirit or scope of the present invention which is limited only by the terms of the appended claims.

What is claimed is:

1. A microchip electrophoretic method of filling a separation passage of a microchip with an electrophoretic buffer solution, injecting a sample into one end and applying a migration voltage across said separation passage for electrophoresis, said method comprising the steps of:

stopping the application of said migration voltage upon complete separation of target components in said sample;

irradiating said separation passage with light over a prescribed range which has separated said target components for repetitive measurement of absorption or light emission by said sample over entire said range; and accumulating measured values in each position of said separation passage for determining migration patterns.

2. A microchip electrophoretic apparatus comprising:

a microchip which has a separation passage formed in a transparent member and is filled with an electrophoretic buffer solution in which a sample is injected into one end and a migration voltage is applied across said separation passage for electrophoresis and separating said sample in said separation passage;

a migration power supply unit which applies said migration voltage across said separation passage;

a means of light irradiation which irradiates said separation passage with light over a prescribed range;

a light detection means which detects said absorption or light emission by sample components being separated in said separation passage; and a data processing/control part which controls said migration power supply unit which stops said application of said migration voltage upon complete separation of said target components in said sample, repetitively performing measurements along said separation passage by said light detection means in this state, thereby accumulating measured signals thereof in each position of said separation passage for determining migration patterns and thereafter performing data processing.

3. The microchip electrophoretic apparatus in accordance with claim 2, wherein said microchip comprises a pair of transparent plate members, a groove for filling a liquid is formed on a surface of at least one of said plate members, one of the said plate members is provided with holes in positions corresponding to said groove, and these plate members are joined together so that said groove faces inward, forming said separation passage.

4. The microchip electrophoretic apparatus in accordance with claim 2, wherein said light irradiation means comprises a light source and an optical system which irradiates said separation passage in a prescribed range with linearly condensed light, said light detection means comprises a plurality of photodetectors which are arranged along said separation passage for simultaneously detecting light from sample components which have been introduced into said separation passage and are irradiated with light by said light irradiation means, and said data processing/control part repetitively performs measurements by said light detection means and accumulates its measuring signals in each said photodetector for determining migration patterns.

5. The microchip electrophoretic apparatus in accordance with claim 4, wherein said light irradiation means comprises said light source which is linearly extended along said separation passage, and a cylindrical lens which is positioned for condensing said light widthwise along said separation passage and for introducing light from said light source into said separation passage, and said light detection means comprises a cylindrical lens positioned for condensing light widthwise along said separation passage and for guiding said light from said separation passage to said photodetectors.

6. The microchip electrophoretic apparatus in accordance with claim 4, wherein said light detection means is adapted to detect light absorption by sample components in said separation passage, and either said light irradiation means or light detection means comprises spectroscopic means which select a wavelength for measuring absorbance.

7. The microchip electrophoretic apparatus in accordance with claim 2, wherein said light irradiation means comprises a light source and an optical system irradiating said separation passage with light beam, said light detection means comprises a single photodetector which is positioned to detect light from said sample in said separation passage by said light from said light irradiation means, a set, which includes said light irradiation means and said light detection means, and said microchip are capable of relative movement along said separation passage, and said data processing/control part which repetitively moves said set or said microchip along said separation passage and accumulates detection signals by said light detection means in each position along said separation passage, thereby obtaining said migration patterns.

8. The microchip electrophoretic apparatus in accordance with claim 7, wherein said light detection means is adapted to detect light absorption by said sample components in said separation passage, and either said light irradiation means or said light detection means comprises spectroscopic means which selects wavelength for measuring absorbance.

9. The microchip electrophoretic apparatus in accordance with claim 2, wherein said data processing/control part comprises a calculation formula which includes a diffusion coefficient of said sample and a peak deterioration degree as parameters for calculating the number of repetitive measurement times by light irradiation in said separation passage, and for automatically calculating said number of repetitive measurement times by inputting said parameters and controlling repetitive measurements.

10. The microchip electrophoretic apparatus in accordance with claim 9, wherein said data processing/control part comprises the following calculation formula for obtaining a time t' until deterioration of a theoretical plate number to N' as a time allowing said repetitive measurement:

$$t' = (L^2/N' - \sigma^2)/2D$$

where L represents a length of said separation passage, σ represents a standard deviation of a peak, and D represents said diffusion coefficient, for calculating said number of repetitive measurement times on the basis of said time t'.

11. The microchip electrophoretic apparatus in accordance with claim 9, wherein said data processing/control part comprises the following calculation formula for obtaining a time t' until deterioration of a theoretical plate number to N' as a time allowing repetitive measurement:

$$t' = L^2(1/N' - 1/N)/2D$$

where L represents a length of said separation passage and D represents said diffusion coefficient, for calculating said number of repetitive measurement times on the basis of said time t'.

* * * * *